United States Patent [19]

Dashefsky

[11] 4,364,399
[45] Dec. 21, 1982

[54] DIAGNOSTIC INSTRUMENT

[76] Inventor: Joseph H. Dashefsky, 100 Manetto Hill Rd., Plainview, N.Y. 11803

[21] Appl. No.: 236,902

[22] Filed: Feb. 23, 1981

[51] Int. Cl.³ .............................................. A61B 5/10
[52] U.S. Cl. ................................................... 128/774
[58] Field of Search ............... 128/774, 348, 645, 652, 128/646–651, 748, 778; 73/78, 79, 85

[56] References Cited

U.S. PATENT DOCUMENTS

| | | | |
|---|---|---|---|
| 2,366,645 | 1/1945 | Ollendorf | 128/651 |
| 2,708,847 | 5/1955 | Esterman | 128/645 |
| 3,272,001 | 9/1966 | Adise | 128/645 |
| 3,677,074 | 7/1972 | Murr | 128/645 |
| 3,738,355 | 6/1973 | Salvatore | 128/774 |
| 3,831,588 | 8/1974 | Rindner | 128/348 X |
| 3,945,373 | 3/1976 | Tweed et al. | 128/778 X |
| 4,159,640 | 7/1979 | Lévéque et al. | 128/774 X |
| 4,325,387 | 4/1982 | Helfer | 128/748 |

OTHER PUBLICATIONS

Fitzgeorge et al., "Engineering in Medicine", vol. 5, No. 4, pp. 105–106, Oct. 1976.

*Primary Examiner*—Lee S. Cohen
*Assistant Examiner*—Angela D. Sykes
*Attorney, Agent, or Firm*—Mark T. Basseches; Paula T. Basseches

[57] ABSTRACT

The present invention is directed to a diagnostic instrument for measuring the deformation resistance of tissue, and particularly the articular surface of the patella. The instrument comprises a cannula adapted to be inserted into end abutting contact with the surface to be measured and a carrier member insertible into the cannula and carrying a pressure sensing device.

9 Claims, 4 Drawing Figures

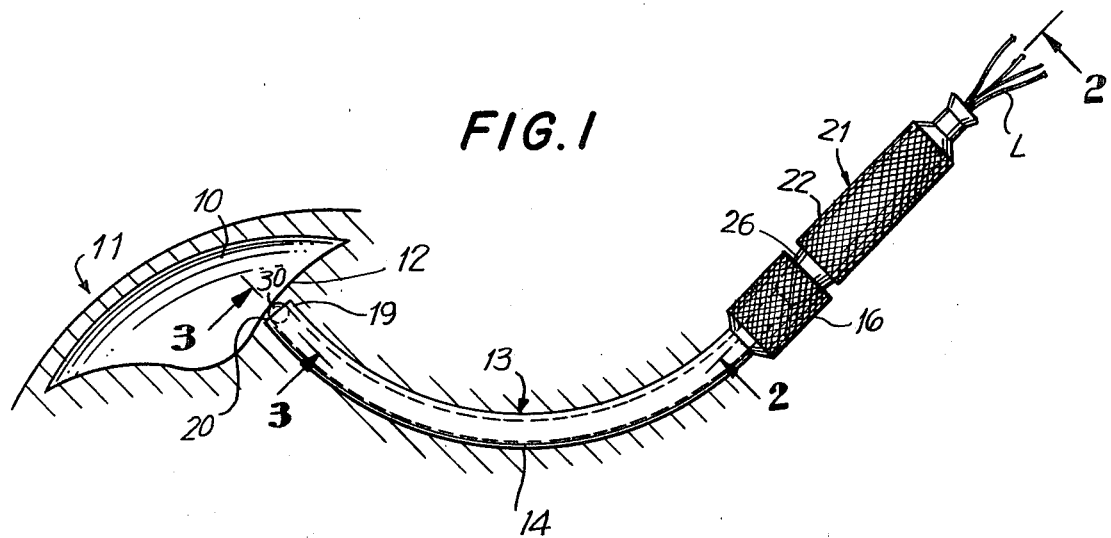
FIG.1
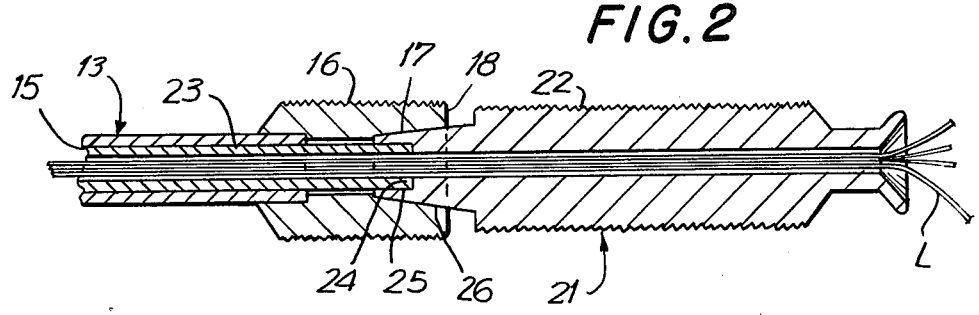
FIG.2
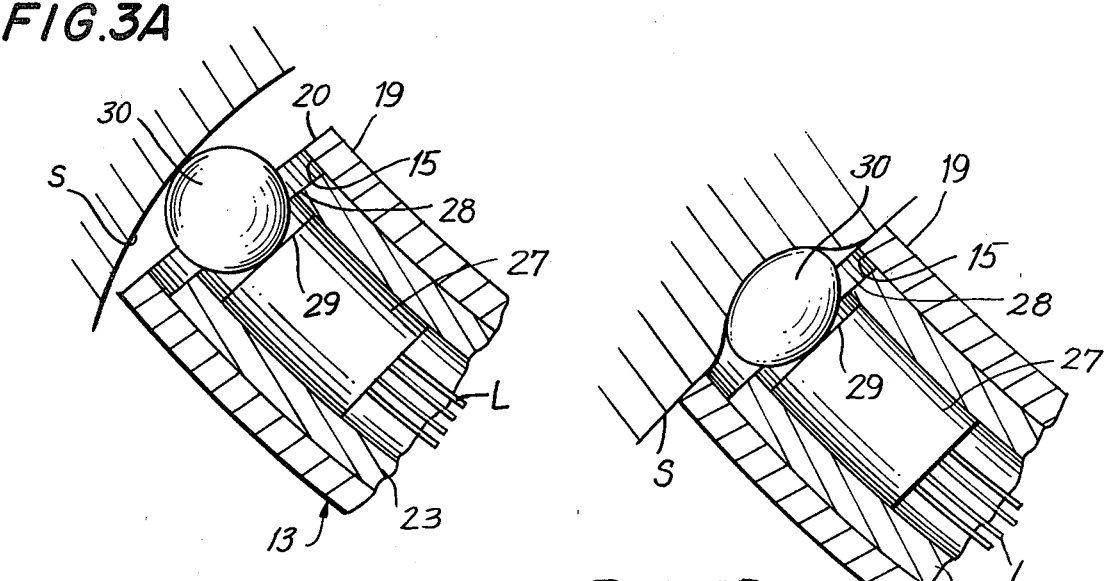
FIG.3A
FIG.3B

DIAGNOSTIC INSTRUMENT

BACKGROUND OF THE INVENTION

1. Field of the Invention

The present invention is in the field of medical diagnostic instrumentation and pertains more particularly to a device for measuring the deformation resistance of certain tissues of the body.

2. The Prior Art

In effecting the diagnosis of certain medical conditions, by way of example and without limitation, chondromalacia patella, it has been prior practice to palpate the articular cartilage, preferably under direct vision, monitored through an arthroscope. An experienced observer may, by judging the indentation resistance, form a judgment as to the existence or non-existence of the subject condition. However, the determination derived by such method is, at best, subjective.

SUMMARY OF THE INVENTION

The present invention is directed to an apparatus for objectively and accurately determining the deformation resistance of internal body tissues, and specifically of the articular cartilage of the patella.

In accordance with the invention, there is provided a cannula having a first stop surface adapted to be engaged against the cartilage surface to be measured. A carrier member is movably mounted in the bore of the cannula, the carrier and cannula having complemental limit stop surfaces whereby the extent of the insertion of the carrier into the cannula may be predictably established.

A pressure sensing transducer is mounted, recessed into and adjacent the distal end of the carrier and a resilient, compressible pressure transmitting member is supported on the lead surface of the transducer.

The spacing of the parts is such as to cause the end portion of the compressible member to project a predetermined amount beyond the stop surface of the cannula when the stop portions of the cannula and carrier are engaged. When the carrier and cannula are in their limit stop engaging position, the lead end of the pressure transmitting member will be engaged against the tissue and force will be exerted against the pressure sensing surface of a transducer mounted on the carrier, the quantum of pressure being a function of the deformation resistance of the tissue.

Electrical leads extending from the transducer are fed to a read-out device which, in turn, provides an objective indication of the deformation resistance of the cartilaginous mass.

It is accordingly an object of the invention to provide a diagnostic instrument for the measurement of the deformation resistance of tissue, such as cartilaginous tissue within the body.

A further object of the invention is the provision of a device of the type described which will, with great accuracy, provide an indication of the deformation resistance of cartilage on a repeatable basis, providing an objective index of the condition of the tissue.

To attain these objects and such further objects as may appear herein or be hereinafter pointed out, reference is made to the accompanying drawings, forming a part hereof, in which:

FIG. 1 is a side elevational view, partly diagrammatic in nature, of a diagnostic apparatus in accordance with the invention, positioned in proximate relation to a tissue mass to be measured;

FIG. 2 is a magnified sectional view taken on the line 2—2 of FIG. 1;

FIGS. 3A and 3B are further magnified fragmentary views of the apparatus, approaching measuring position and in measuring position, respectively.

Turning now to the drawings, there is shown in FIG. 1, in diagrammatic fashion, a representation of the patella 10 of the knee. The softness or hardness of the cartilage layer 12 of the articular surface of the patella is an indication of the presence of chondromalacia patella, and accurate measurement of such condition provides an important element in the determination of the advisability of effecting corrective surgery.

An apparatus for objectively effecting such determination is disclosed in the figures, such apparatus comprising generally a cannula 13 which optionally but preferably is comprised of an arcuate body portion 14 having an internal bore 15 formed therein, and terminating in a knurled collar member 16.

The collar member 16 preferably includes a frusto-conic recess 17 extending inwardly from the outermost end 18 of the collar. The distal end 19 of the cannula terminates in a blunt stop surface 20.

An insert member 21 is provided, the insert member including a knurled handle portion 22, to which is fixed an arcuate body portion 23 joined to the handle 22, for which purpose the end portion 24 of the carrier is received in a bore portion 25 in the handle.

The outer peripheral lead portion 26 of the handle 22 is of a complemental frusto-conic configuration, matching the configuration of the recess 17, whereby the frusto-conic portion 26 may be inserted into the recess 17 until a reference or stop position between the respective parts is achieved.

Preferably, the complementally formed frusto-conic parts together define a frictional interfit which will retain the insert in a locked reference or "reading" position relative to the cannula.

The body portion 23 of the insert 21 is of arcuate configuration, matching the radius of curvature of the bore of the cannula, whereby the same may be readily inserted into such bore through the bore 15 of the cannula.

A pressure sensing transducer 27 is lodged within the carrier body 23 at a position slightly recessed from the distal end 28 of the carrier—see FIGS. 3A and 3B. The transducer 27 includes a pressure sensing surface portion 29, to which surface is bonded an elastomeric or like resilient pressure transmitting member 30.

The transmitting member optionally but preferably is formed of a sterilization temperature resistant elastomer, a suitable such elastomer being sold under the trading name SILASTIC.

Optionally but preferably, the pressure transmitting member 30 may be spherical in configuration.

The dimensions of the components are such as to provide an annular clearance area surrounding the pressure transmitting member 30 between such member and the inner bore 15 of the cannula. The member 30 is thus permitted to expand radially without interference from the cannula or the insert.

Without limitation and for purposes of illustration only, a suitable pressure sensing transducer operating on a piezo resistive principle is manufactured by Kulite Semiconductor Products of Ridgefield, New Jersey and is identified by such organization as its Model XTM-19-

100. It will be understood that other pressure sensing transducers operating on other than piezo resistive principles may be suitably employed.

The transducer identified has a diameter of 0.147" and is thus, by virtue of its small size, ideally suited for use as a measuring mechanism.

The outleads L emanating from the transducer may be fed to a suitable measuring apparatus, such as an ohmmeter, with or without an auxiliary Wheatstone bridge adapter. The specific read-out mechanism employed forms no part of the present invention and it will be readily recognized that the nature of the read-out apparatus will depend upon the sensing member of the transducer device employed.

Optionally but preferably, the SILASTIC sphere 30 is formed of a color clearly contrasting with the color of the tissue being tested and also with the color of the cannula.

The manner of use of the device will be briefly described.

An arthroscope is initially inserted into the joint adjacent the area of tissue to be measured, thereby providing for direct visual observation of the deployment of the diagnostic instrument. The cannula member 13 is inserted into position adjacent the arthroscope and in opposed relation to the tissue surface to be measured. Insertion of the cannula is effected, as is typical, by initially emplacing an arcuate trocar in the bore of the cannula and effecting an incision.

After the incision is made and the end of the cannula introduced into the body adjacent the joint, the trocar is removed and an obturator substituted therefor. The cannula and obturator are maneuvered through the joint and into proximate relation to the tissue to be measured, following which the obturator is removed and the carrier member 21 substituted therefor.

The blunt reference surface of the cannula is maneuvered into engagement with the tissue to be measured, utilizing positioning information derived by reference to the arthroscope, the end portion 20 preferably being disposed perpendicular to the tissue surface, as shown in FIG. 3B. The insert member is forced into the cannula such that the complemental stop surfaces 17 and 26 are in their reference or stop positions.

It will be understood that the cannula and insert member may be adjusted to the reference or stop position before or after the stop surface 20 of the cannula is engaged against the surface S of the tissue to be measured.

As is shown diagrammatically in FIG. 3B, when the parts are positioned in their reference or measuring condition, the surface S will be indented and the pressure transmitting member 30 will be deformed, applying to the sensing surface 29 of the transducer 27 a pressure which is a function of the deformation resistance of the tissue or cartilage.

The read-out mechanism, when the parts are positioned as shown in FIG. 3B, will thereby provide a numerical value which is an accurate indication of the deformation resistance of the tissue.

From the foregoing it will be apparent that there is shown and described a diagnostic instrument adapted to be employed predictably and repeatably to measure the deformation resistance of tissue masses within the body.

While the device has been illustrated in connection with the measurement of the articular surface of the cartilage of the patella, it will be readily recognized that by suitably selecting the transducer for an anticipated pressure range and preferably also selecting the deformation resistance of the pressure transmitting member 30, the device may be readily accommodated to measuring the deformation resistance of other body tissues.

It will be further understood that while the configuration of the nesting parts has been illustrated as arcuate, since such configuration is particularly useful in examining the tissue of the knee joint, the invention is not to be considered to be limited to such configuration except as may otherwise be provided in the claims.

Numerous other details of construction will occur to those skilled in the art and familiarized with the instant disclosure. Accordingly the invention is to be broadly construed within the scope of the appended claims.

Having thus described the invention and illustrated its use, what is claimed as new and is desired to be secured by Letters Patent is:

1. An instrument for measurement of the deformation resistance of cartilaginous tissue, such as the articular surface of the cartilage of the patella comprising, in combination, a cannula having a bore, said cannula having a first end portion defining a blunt stop surface, a carrier member movably mounted in said bore and including a sensing end portion and a manipulation end portion, complemental limit stop means formed on said cannula and carrier member positioned to engage at a limiting inserted position of said sensing end portion of said carrier member into said cannula and to block further relative movements of said parts in the direction of insertion of said carrier member, a pressure sensing transducer mounted in said carrier member adjacent said sensing end portion, said transducer including a pressure sensing surface at a lead portion thereof, said pressure sensing surface, at said limiting inserted position of said carrier member being disposed within said cannula in proximate spaced relation to said stop surface, and a resilient, compressible pressure transmission member mounted on said pressure sensing surface of said transducer, said transmission member, in said limiting inserted position, projecting a predetermined distance beyond said stop surface.

2. An instrument in accordance with claim 1 wherein said pressure transmission member is comprised of elastomeric material.

3. An instrument in accordance with claim 2 wherein said pressure transmission member is formed of a material of a color contrasting with the color of said cannula.

4. An instrument in accordance with claim 3 wherein said pressure transmission member is generally spherical in configuration.

5. An instrument in accordance with claim 4 wherein clearance areas are defined between said pressure transmission member and said cannula, thereby to permit lateral expansion of said pressure transmission member.

6. An instrument in accordance with claim 1 wherein said cannula and carrier member are arcuate in longitudinal section.

7. An instrument in accordance with claim 1 wherein said transducer comprises a piezo-resistive material.

8. An instrument in accordance with claim 1 wherein said cannula and carrier member include locking means for retaining said carrier member in said limited inserted position within said cannula.

9. An instrument in accordance with claim 8 wherein said locking means comprise frictional interfitting portions of said cannula and carrier member.

* * * * *